United States Patent

Zimmermann et al.

[11] Patent Number: 5,516,775
[45] Date of Patent: May 14, 1996

[54] FURTHER USE OF PYRIMIDINE DERIVATIVES

[75] Inventors: Jürg Zimmermann, Möhlin; Giorgio Caravatti, Allschwil, both of Switzerland

[73] Assignee: Ciba-Geigy Corporation, Tarrytown, N.Y.

[21] Appl. No.: 103,493

[22] Filed: Aug. 6, 1993

[30] Foreign Application Priority Data

Aug. 31, 1992 [CH] Switzerland ............... 2729/92

[51] Int. Cl.⁶ .................. A61K 31/505; A61K 31/54; A61K 31/535; A61K 31/53
[52] U.S. Cl. .................. 514/224.2; 514/235.8; 514/241; 514/255; 514/275
[58] Field of Search ............... 514/275, 224.2, 514/235.8, 241, 255

[56] References Cited

U.S. PATENT DOCUMENTS

| | | | |
|---|---|---|---|
| 4,816,450 | 3/1989 | Bell et al. | 514/25 |
| 4,876,252 | 10/1989 | Torley et al. | 514/224.8 |

FOREIGN PATENT DOCUMENTS

| | | |
|---|---|---|
| 0164204 | 12/1985 | European Pat. Off. . |
| 0233461 | 8/1987 | European Pat. Off. . |
| 0453731 | 2/1991 | European Pat. Off. . |

*Primary Examiner*—Allen J. Robinson
*Assistant Examiner*—Mary C. Cebulak
*Attorney, Agent, or Firm*—Karen G. Kaiser

[57] ABSTRACT

The invention relates to the use of known N-phenyl-2-pyrimidine derivatives for inhibiting proteinkinase C in warm-blooded animals as antitumor agents.

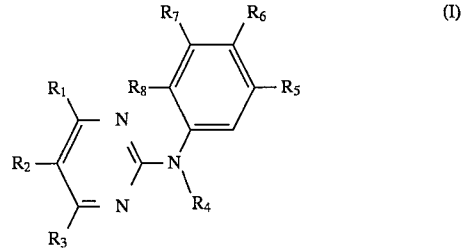

The substituents in formula I are as defined in claim 1.

11 Claims, No Drawings

FURTHER USE OF PYRIMIDINE DERIVATIVES

The present invention relates to the use of known N-phenyl-2-pyrimidine derivatives for inhibiting protein kinase C and/or as antitumour agents, and also for the preparation of pharmaceutical compositions for use as inhibitors of protein kinase C and/or as antitumour agents in warm-blooded animals.

European patent application filed under number 87100277.0 and published on Aug. 26, 1987 under publication number 0 233 461, and which is partially equivalent to U.S. Pat. No. 4,876,252, discloses N-phenyl-2-pyrimidinamine derivatives, their preparation and use as antiasthmatic and antiallergic agents owing to their inhibition of histamine release, as well as their use for treating inflammatory conditions and diabetes.

The present invention is based on the observation that some of the N-phenyl-2-pyrimidinamine derivatives disclosed in EP-A-0 233 461 selectively inhibit the protein kinase C enzyme.

Protein kinase C, which is dependent on phospholipids and calcium, occurs within cells in a number of species (distribution of the species tissue-specific) and participates in various fundamental processes such as signal transmission, proliferation and differentiation, as well as the release of hormones and neurotransmitters. This enzyme is activated either by receptor-mediated hydrolysis of phospholipids of the cell membrane or by direct interaction with specific rumour-promoting substances. Cellular functions which are controlled by protein kinase C can be influenced by modulation of the enzymatic activity of protein kinase C.

Specifically, the invention relates to the use of N-phenyl-2-pyrimidinamine derivatives of formula

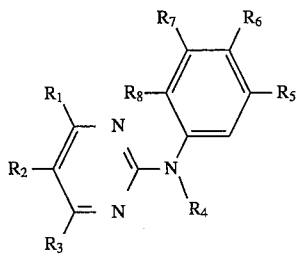 (I)

wherein $R_1$ is hydrogen or $C_1$–$C_3$alkyl, $R_2$ is hydrogen or $C_1$–$C_3$alkyl, $R_3$ is 2-pyridyl, 3-pyridyl, 4-pyridyl, 2-methyl-3-pyridyl, 4-methyl-3-pyridyl, 2-furyl, 5-methyl-2-furyl, 2,5-dimethyl-3-furyl, 2-thienyl, 3-thienyl, 5-methyl-2-thienyl, 2-phenothiazinyl, 4-pyrazinyl, 2-benzofuryl, N-oxido-2-pyridyl, N-oxido-3-pyridyl, N-oxido-4-pyridyl, 1H-indol-2-yl, 1H-indol-3-yl, 1-methyl-1H-pyrrol-2-yl, 4-quinolinyl, 1-methyl-pyridinium- 4-yliodide, dimethylaminophenyl or N-acetyl-N-methyl-aminophenyl, $R_4$ is hydrogen, $C_1$–$C_3$alkyl, —CO—CO—O—$C_2H_5$ or N,N-dimethylaminoethyl, at least one of $R_5$, $R_6$, $R_7$ and $R_8$ is $C_1$—$C_6$alkyl, $C_1$–$C_3$alkoxy, chloro, bromo, iodo, trifluoromethyl, hydroxy, phenyl, amino, mono($C_1$—$C_3$-alkyl)amino, di($C_1$–$C_3$alkyl)amino, $C_2$—$C_4$alkanoyl, propenyloxy, carboxy, carboxymethoxy, ethoxycarbonylmethoxy, sulfanilamido, N,N-di($C_1$–$C_3$alkyl)sulfanilamido, N-methylpiperazinyl, piperidinyl, 1H-imidazol-1-yl, 1H-triazol-1-yl, 1H-benzimidazol-2-yl, 1-naphthyl, cyclopentyl, 3,4-dimethylbenzyl or a radical of one of the formulae:

—$CO_2R$, —NH—C(=O)—R, —N(R)—C(=O)—R,
—O—($CH_2$)$_n$—N(R)—R, —C(=O)—NH—($CH_2$)$_n$—N(R)—R, —CH($CH_3$)—NH—CHO, —C($CH_3$)=N—OH,
—C($CH_3$)=N—O—$CH_3$, —C($CH_3$)—$NH_2$, —NH—$CH_2$—

C(=O)—N(R)—R,

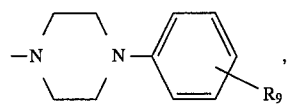

—($CH_2$)$_m$—$R_{10}$, —X—($CH_2$)$_m$—$R_{10}$ or

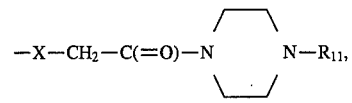

wherein R is $C_1$–$C_3$alkyl, X is oxygen or sulfur, m is 1, 2 or 3, n is 2 or 3, $R_9$ is hydrogen, $C_1$–$C_3$alkyl, $C_1$–$C_3$alkoxy, chloro, bromo, iodo or trifluoromethyl, $R_{10}$ is 1H-imidazol-1-yl or morpholinyl, and $R_{11}$ is $C_1$–$C_3$alkyl or unsubstituted phenyl or phenyl which is monosubstituted by $C_1$–$C_3$alkyl, halogen or trifluoromethyl, and the remaining of the substituents $R_5$, $R_6$, $R_7$ and $R_8$ are hydrogen, or of pharmaceutically acceptable salts of said compounds containing at least one salt-forming group, for inhibiting protein kinase C and for the preparation of pharmaceutical compositions for use as inhibitors of protein kinase C in warm blooded animals. The novel use of the compounds of formula I as inhibitors of protein kinase C does not extend to their prior claimed use for the treatment of asthma, allergies, inflammatory conditions and diabetes, even if the activity against these diseases should be attributable to the inhibition of protein kinase C.

The compounds of formula I and their preparation are disclosed in EP-A-0 233 461 and in U.S. Pat. 4,876,252.

Salt-forming groups in a compound of formula I are groups or radicals having basic or acidic properties. Compounds having at least one basic group or at least one basic radical, for example a free amino group, a pyrazinyl radical or a pyridyl radical, can form acid addition salts, conveniently with inorganic acids such as hydrochloric acid, sulfuric acid or a phosphoric acid, or with suitable organic carboxylic or sulfonic acids, typically aliphatic mono- or dicarboxylic acids such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids such as benzoic acid, 2-phenoxybenzoic acid, 2-acetoxybenzoic acid, salicylic acid, 4-aminosalicylic acid, aromatic-aliphatic carboxylic acids such as mandelic acid or cinnamic acid, heteroaromatic carboxylic acids such as nicotinic acid or isonicotinic acid, aliphatic sulfonic acids such as methanesulfonic acid, ethanesulfonic acid or 2-hydroxyethane-sulfonic acid, or aromatic sulfonic acids such as benzenesulfonic acid, p-toluenesulfonic acid or naphthalene-2-sulfonic acid. When several basic groups are present, mono- or polyacid addition salts may be formed.

Compounds of formula I having acidic groups, for example a free carboxyl group, can form metal or ammonium salts such as alkali metal or alkaline earth metal salts, typically sodium, potassium, magnesium or calcium salts, or ammonium salts with ammonia or suitable organic amines such as tertiary monoamines, typically triethylamine or tris(2-hydroxyethyl)amine, or heterocyclic bases such as N-ethylpiperidine or N,N'-dimethylpiperazine.

It has now been found that the compounds of formula I have valuable pharmacological properties that were previously unknown. Inter alia, they selectively inhibit the protein kinase C enzyme.

Protein kinase C from pig brain is used to determine the inhibitory action on protein kinase C. The inhibitory action of the compounds of formula I on protein kinase C is determined by the method of D. Fabbro et al, as described in Example 2. In this assay, the compounds of formula I inhibit protein kinase C even at a concentration $IC_{50}$ in the range from c. 0.1 to 30 μmol/liter.

In contradistinction thereto, the compounds of formula I only inhibit other enzymes, for example protein kinase A and phosphorylase protein kinase, at far higher concentration, for example 100 times higher. This distinction demonstrates the selectivity of the compounds of formula I.

Owing to their inhibitory action on protein kinase C, the compounds of formula I and their pharmaceutically acceptable salts can be used as tumour-inhibiting, immunomodulating and anti-bacterial drugs and, further, as drugs against atherosclerosis, the immunodeficiency disease AIDS, and diseases of the cardiovascular system and the central nervous system.

As may already be expected in the light of the inhibitory action on protein kinase C described above, the compounds of formula I have antiproliferative properties which can be demonstrated direct, inter alia, in the assay described in Example 1. In this assay, the inhibitory action of compounds of formula I on the growth of human T24 bladder carcinoma cells is determined. The $IC_{50}$ values obtained for the compounds of formula I are from c. 1 to 10 μmol/liter.

The antiproliferative properties can also be demonstrated in vivo, as described in Example 3. In the assay described in Example 3, the compounds of formula I, when administered perorally or intraperitoneally, reduce tumour volume to about 35–70% of tumour volume in control animals treated with placebo.

Owing to the described properties, the compounds of formula I can be used in particular as tumour-inhibiting agents, inter alia for the treatment of tumours of the bladder. The invention relates to this utility of the compounds of formula I as antitumour agents irrespective of whether the antitumour activity is directly attributable to the inhibition of protein kinase C or not, and irrespective of whether it can be proved that the antitumour activity is directly attributable to the inhibition of protein kinase C.

Use of the compounds of formula I in cancer therapy in conjunction with other chemotherapeutic agents prevents the development of resistance (multidrug resistance) or they neutralise an already existing resistance to the other chemotherapeutic agents. In addition, the compounds of formula I are suitable for the other utilities mentioned in connection with protein kinase C modulators, and they can be used in particular for the treatment of diseases that respond to inhibition of protein kinase C. The invention relates to the use of the compounds of formula I for the purposes cited above, with the exception of their prior claimed use against asthma, allergies, inflammatory conditions and diabetes, and for the preparation of pharmaceutical compositions for use for this purpose.

It is preferred to use compounds of formula I, wherein at least two of $R_5$, $R_6$ and $R_8$ are each hydrogen, more particularly those compounds wherein $R_5$, $R_6$ and $R_8$ are each hydrogen and the other substituents are as previously defined, and pharmaceutically acceptable salts of said compounds containing at least one salt-forming group.

Principally, compounds of formula I are used wherein $R_1$, $R_2$, $R_4$, $R_5$, $R_6$ and $R_8$ are each hydrogen, $R_3$ is 2-pyridyl, 3-pyridyl, 4-pyridyl, 2-methyl-3-pyridyl, 4-methyl-3-pyridyl, 2-furyl, 5-methyl-2-furyl, 2,5-dimethyl-3-furyl, 2-thienyl, 3-thienyl, 5-methyl-2-thienyl, 2-phenothiazinyl, 4-pyrazinyl, 2-benzofuryl, N-oxido-2-pyridyl, N-oxido-3-pyridyl, N-oxido-4-pyridyl, 1H-indol-2-yl, 1H-indol-3-yl, 1-methyl-1H-pyrrol-2-yl, 4-quinolinyl, 1-methylpyridinium-4-yliodide, dimethylaminophenyl or N-acetyl-N-methylaminophenyl, and $R_7$ is $C_1$–$C_6$alkyl, $C_1$–$C_3$alkoxy, chloro, bromo, iodo, trifluoromethyl, hydroxy, phenyl, amino, mono($C_1$–$C_3$alkyl)-amino, di($C_1$–$C_3$alkyl)amino, $C_2$–$C_4$alkanoyl, propenyloxy, carboxy, carboxymethoxy, ethoxycarbonylmethoxy, sulfanilamido, N,N-di($C_1$–$C_3$alkyl)sulfanilamido, N-methylpiperazinyl, piperidinyl, 1H-imidazol-1-yl, 1H-triazol-1-yl, 1H-benzimidazol-2-yl, 1-naphthyl, cyclopentyl, 3,4-dimethylbenzyl or a radical of one of the formulae:

—$CO_2R$, —NH—C(=O)—R, —N(R)—C(=O)—R,
—O—$(CH_2)_n$—N(R)—R, —C(=O)—NH—$(CH_2)_n$—N(R)—R, —CH($CH_3$)—NH—CHO, —C($CH_3$)=N—OH,
—C($CH_3$)=N—O—$CH_3$, —C($CH_3$)—$NH_2$, —NH—$CH_2$—C(=O)—N(R)—R,

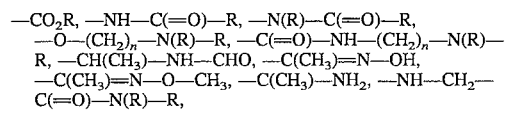

—$(CH_2)_m$—$R_{10}$, —X—$(CH_2)_m R_{10}$ or

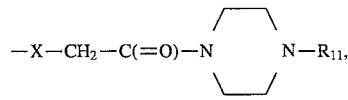

wherein R is $C_1$–$C_3$alkyl, X is oxygen or sulfur, m is 1, 2 or 3, n is 2 or 3, $R_9$ is hydrogen, $C_1$–$C_3$alkyl, $C_1$–$C_3$alkoxy, chloro, bromo, iodo or trifluoromethyl, $R_m$ is 1H-imidazol-1-yl or morpholinyl, and $R_{11}$ is $C_1$–$C_3$alkyl or unsubstituted phenyl or phenyl which is monosubstituted by $C_1$–$C_3$alkyl, halogen or trifluoromethyl, or of pharmaceutically acceptable salts of said compounds containing at least one salt-forming group.

It is especially preferred to use compounds of formula I, wherein $R_1$, $R_2$, $R_4$, $R_5$, $R_6$ and $R_8$ are each hydrogen, $R_3$ is 3-pyridyl, and $R_7$ is 1H-imidazol-1-yl, amino, trifluoromethyl, chloro or a radical of formula —$CO_2R$ or —C(=O)—NH—$(CH_2)_n$—N(R)—R, wherein each R is hydrogen or methyl and n is 3, and pharmaceutically acceptable acid addition salts of said compounds.

It is most preferred to use the compounds of formula I cited in the Examples and pharmaceutically acceptable acid addition salts of said compounds.

The invention also relates to a method of treating warm-blooded animals suffering from a tumoral disease, which comprises administering to warm-blooded animals in need of such treatment an effective, tumour-inhibiting amount of a compound of formula I or of a pharmaceutically acceptable salt thereof. The invention further relates to the use of a compound of formula I or of a pharmaceutically acceptable salt thereof for inhibiting protein kinase C in warm-blooded animals or for the preparation of pharmaceutical compositions for use in the therapeutic treatment of the human or animal body. The invention also relates to a method of inhibiting protein kinase C in warm-blooded animals, which comprises administering to a warm-blooded animal in need of such treatment an effective, protein kinase C inhibiting amount of a compound of formula I. It is contemplated that, depending on the species, age, individual condition, mode of administration and the particular clinical picture, daily doses of c. 1–2000 mg, preferably 50–2000 mg, more particularly 500–2000 mg, typically 500–1000 mg, will be administered enterally or parenterally to a warm-blooded animal of 70 kg body weight.

The invention also relates to the use of a compound of formula I or a pharmaceutically acceptable salt thereof for the preparation of pharmaceutical compositions for use for inhibiting the protein kinase C, inter alia for the treatment of tumour-induced diseases. The novel pharmaceutical compositions contain an effective amount of the active compound, preferably an amount effective for the prophylaxis or therapy of one of the aforementioned dfiseases, together with pharmaceutically acceptable carriers that are suitable for topical, enteral, for example oral or rectal, or parenteral administration, and which may be inorganic or organic, solid or liquid. For oral administration it is preferred to use tablets or gelatin capsules that contain the active compound together with a diluent such as lactose, dextrose, suchrose, mannitol, sorbitol, cellulose and/or glycerol, and/or glidants, typically diatomaceous earth, talcum, stearic acid or salts thereof such as magnesium or calcium stearate, and/or polyethylene glycol. Tablets may also contain binders such as magnesium aluminium silicate, starches such as maize, corn or rice starch, gelatin, methyl cellulose, sodium carboxymethyl cellulose and/or polyvinyl pyrrolidone and, if desired, disintegrators such as starches, agar, alginic acid or a salt thereof, e.g. sodium alginate, and/or effervescent mixtures, or absorbents, colorants, flavourings and sweeteners. The pharmacologically active compounds of this invention can also be used in the form of compositions for parenteral administration or of infusion solutions. Such solutions are preferably isotonic aqueous solutions or suspensions which, in the case of lyophilised compositions that contain the active compound by itself or together with a carrier such as mannitol, can be prepared before use. The pharmaceutical compositions can be sterilised and/or can contain adjuvants such as preservatives, stabilisers, wetting agents and/or emulsifiers, solubilisers, salts for regulating the osmotic pressure and/or buffers. The novel pharmaceutical compositions which, if desired, may contain further pharmacologically active substances such as antibiotics, are prepared in per se known manner by conventional mixing, granulating, sugar-coating, solution or lyophilising methods and contain from about 1% to 100%, preferably from about 1% to about 20%, of active compound.

The invention is illustrated by the following non-limitative Examples.

ABBREVIATIONS compound A=N-(3-1H-imidazol-1-ylphenyl)-4-(3-pyridyl)-2-pyrimidinamine (=compound of formula I, wherein $R_1$, $R_2$, $R_4$, $R_5$, $R_6$ and $R_8$ are each hydrogen, $R_3$ is 3-pyridyl and $R_7$ is 1H-imidazol-1-yl)

compound B=N-(3-trifluoromethylphenyl)-4-(3-pyridyl)-2-pyrimidinamine compound C=N-(3-chlorophenyl)-4-(3-pyridyl)-2-pyrimidinamine compound D=N-(3-aminophenyl)-4-(3-pyridyl)-2-pyrimidinamine compound E=N-(3-methoxycarbonylphenyl)-4-(3-pyridyl)-2-pyrimidinamine compound F=N-(3-[3-aminopropylaminocarbonyl]phenyl)-4-(3-pyridyl)-2-pyrimidinamine

EXAMPLE 1

Inhibition of the Growth of Human Bladdder Carcinoma Cells

Human T24 bladder carcinoma cells are incubated in "Eagle's minimal essential medium", to which 5% (v/v) foetal calf serum has been added, in a humidified incubator at 37° C. and 5 percent by volume $CO_2$ in air. The carcinoma cells (1000–1500) are inoculated in 96-well microtitre plates and incubated overnight under the stated conditions. The test compound is added in serial dilutions on day 1. The plates are incubated for 5 days under the stated conditions. During this time the control cultures undergo at least 4 cell divisions. After incubation, the cells are fixed with a 3.3% (g/v) aqueous solution of glutaraldehyde, washed with water and stained with a 0.05% (weight/volume) aqueous solution of methylene blue. After washing, the stain is eluted with 3% (g/v) aqueous hydrochloric acid. Afterwards, the optical density (OD) per well, which is directly proportional to the number of cells, is measured with a photometer (Titertek multiskan) at 665 nm. The $IC_{50}$ values are computed by a computer system, using the formula $$\frac{OD_{665}(\text{test}) \text{ minus } OD_{665}(\text{start})}{OD_{665}(\text{control}) \text{ minus } OD_{665}(\text{start})} \times 100$$

The $IC_{50}$ values are defined as that active compound concentration at which the number of cells per well at the end of the incubation period is only 50% of the number of cells in the control cultures. The following $IC_{50}$ values are obtained in this assay for the compounds of formula I:

| compound | [μmol/litre] |
| --- | --- |
| A | 2.5 |
| B | 7.4 |
| C | 5.2 |
| D | 7.2 |

EXAMPLE 2

Determination of the Inhibitory Action on Protein Kinase C

Protein kinase C from pig brain. purified in accordance with the procedure described by T. Uchida and C. R. Filbum in J. Biol. Chem. 259, 12311–4 (1984) is used to determine the inhibitory action on protein kinase C. The inhibitory action of the compounds of formula I on protein kinase C is determined by the method of D. Fabro et al., Arch. Biochem. Biophys. 239, 102–111 (1985). The following $IC_{50}$ values are obtained in this assay for the compounds of formula I:

| compound | [μmol/litre] |
| --- | --- |
| A | 8.8 |
| B | 2.5 |
| C | 6.3 |
| D | 28 |
| E | 26 |
| F | 28 |

EXAMPLE 3

Antitumour Activity in Mice

On day 0 a c. 25 mg piece of human T24 bladder carcinoma is transplanted subcutaneously using Trokar under operable "forene" narcosis on female Balb/c nude mice (Balb/c(Balb/c nu/nu, Bomholdgaard, Denmark; six mice per group). On day 6 after the tumour transplantation the average tumour volume is 120–140 mm³ and treatment is commenced. The treatment consists in administering perorally or intraperitoneally once daily over 15 successive days, i.e. altogether 15 times, 25 ml/kg of the following formulation. This formulation is prepared as follows: 16 mg of a compound of formula I are dissolved in 0.4 ml of dimethyl sulfoxide (100%). Then 0.05 ml of Tween 80 is added to this solution and the batch is mixed. Then 7.6 ml of a 0.9% aqueous solution of sodium chloride are added and the batch is thoroughly mixed. This formulation is prepared fresh daily. The control animals receive a placebo. The placebo is the same formulation without compound of formula I.

24 hours after the last administration, the tumour volume is measured and the ratio [%] of the tumour volume T/C is determined in the treated animals (T) and the control animals treated with placebo (C). The tumour volume in the control animals is defined as 100%, i.e. the smaller the ratio T/C the more effective the formulation.

A ratio T/C of 68% and 53% is obtained after peroral administration of 25 and 50 mg, respectively, of compound B as active ingredient in the above assay. A ratio T/C of 54% and 46% is obtained after intraperitoneal administration of 25 and 50 mg, respectively, of compound B.

EXAMPLE 4

Tablets comprising 20 mg of active ingredient, e.g. one of the compounds of formula I described in Examples 1–2 and having the following composition, are prepared in conventional manner:

| Composition: | |
|---|---|
| active ingredient | 20 mg |
| wheat starch | 60 mg |
| lactose | 50 mg |
| colloidal silicic acid | 5 mg |
| talcum | 9 mg |
| magnesium stearate | 1 mg |
| | 145 mg |

Preparation: The active ingredient is mixed with a portion of the wheat starch, with the lactose and the colloidal silicic acid and the mixture is forced through a sieve. A further portion of the wheat starch is made into a paste, on a water bath, with five times the amount of water and the powder mixture is kneaded with the paste until a slightly plasticised mass is obtained.

The plasticised mass is passed through a sieve of c. 3 mm mesh size and dried, and the resulting dry granulate is again passed through a sieve. Then the remainder of the wheat starch, the talc and the magnesium stearate are blended in and the mixture is compressed to 145 mg tablets with a breaking notch.

EXAMPLE 5

Tablets comprising 1 mg of active ingredient, e.g. one of the compounds of formula I described in Examples 1–2 and having the following composition, are prepared in conventional manner:

| Composition: | |
|---|---|
| active ingredient | 1 mg |
| wheat starch | 60 mg |
| lactose | 50 mg |
| colloidal silicic acid | 5 mg |
| talcum | 9 mg |
| magnesium stearate | 1 mg |
| | 126 mg |

Preparation: The active ingredient is mixed with a portion of the wheat starch, with the lactose and the colloidal silicic acid and the mixture is forced through a sieve. A further portion of the wheat starch is made into a paste, on a water bath, with five times the amount of water and the powder mixture is kneaded with the paste until a slightly plasticised mass is obtained.

The plasticised mass is passed through a sieve of about 3 mm mesh size and dried, and the resulting dry granulate is again passed through a sieve. Then the remainder of the wheat starch, the talc and the magnesium stearate are blended in and the mixture is compressed to 126 mg tablets provided with a breaking notch.

EXAMPLE 6

Capsules comprising 10 mg of active ingredient, e.g. one of the compounds of formula I described in Examples 1–2 are prepared in conventional manner as follows:

| Composition: | |
|---|---|
| active ingredient | 2500 mg |
| talcum | 200 mg |
| colloidal silicic acid | 50 mg |

Preparation: The active ingredient is intimately mixed with the talcum and the colloidal silicic acid and the mixture is forced through a sieve of 0.5 mm mesh size and then filled in 11 mg portions into hard gelatin capsules of suitable size.

What is claimed is:

1. A method of treatment of warm-blooded animals suffering from a protein kinase C dependent tumoral disease, which comprises treating warm-blooded animals in need of such treatment with an effective tumor-inhibiting amount of a compound of formula I

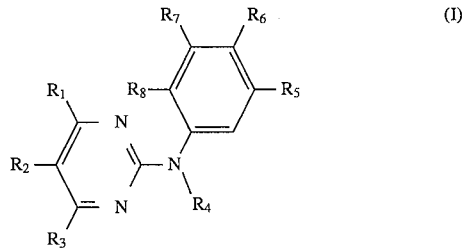

wherein $R_1$ is hydrogen or $C_1$–$C_3$alkyl, $R_2$ is hydrogen or $C_1$–$C_3$alkyl, $R_3$ is 2-pyridyl, 3-pyridyl, 4-pyridyl, 2-methyl-3-pyridyl, 4-methyl-3-pyridyl, 2-furyl, 5-methyl-2-furyl, 2,5-dimethyl-3-furyl, 2-thienyl, 3-thienyl, 5-methyl-2-thienyl, 2-phenothiazinyl, 4-pyrazinyl, 2-benzofuryl, N-oxido-2-pyridyl, N-oxido-3-pyridyl, N-oxido-4-pyridyl, 1H-indol-2-yl, 1H-indol-3-yl, 1-methyl-1H-pyrrol-2-yl, 4-quinolinyl, 1-methyl-pyridinium-4-yliodide, dimethylaminophenyl or N-acetyl-N-methylaminophenyl, $R_4$ is hydrogen, $C_1$–$C_3$alkyl, —CO—CO—O—$C_2H_5$ or N,N-dimethylaminoethyl, at least one of $R_5$, $R_6$, $R_7$ and $R_8$ is $C_1$–$C_6$alkyl, $C_1$–$C_3$alkoxy, chloro, bromo, iodo, trifluoromethyl, hydroxy, phenyl, amino, mono-($C_1$–$C_3$-alkyl)amino, di($C_1$-$C_3$alkyl)amino, $C_2$-$C_4$alkanoyl, propenyloxy, carboxy, carboxymethoxy, ethoxycarbonylmethoxy, sulfanilamido, N,N-di($C_1$-$C_3$alkyl)sulfanilamido, N-methylpiperazinyl, piperidinyl, 1H-imidazol-1-yl, 1H-triazol-1-yl, 1H-benzimidazol-2-yl, 1-naphthyl, cyclopentyl, 3,4-dimethylbenzyl or a radical of one of the formulae:

—$CO_2$R, —NH—C(=O)—R, —N(R)—C(=O)—R, —O—($CH_2$)$_n$—N(R)—R, —C(=O)—NH—($CH_2$)$_n$—N(R)—R, —CH($CH_3$)—NH—CHO, —C($CH_3$)=N—OH, —C($CH_3$)=N—O—$CH_3$, —C($CH_3$)—$NH_2$, —NH—$CH_2$—C(=O)—N(R)—R,

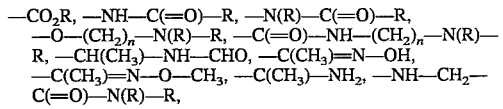

—($CH_2$)$_m$—$R_{10}$, —X—($CH_2$)$_m$—$R_{10}$ or

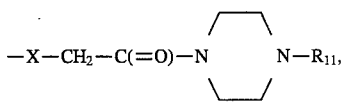

wherein R is $C_1$-$C_3$alkyl, X is oxygen or sulfur, m is 1, 2 or 3, n is 2 or 3, $R_9$ is hydrogen, $C_1$-$C_3$alkyl, $C_1$-$C_3$alkoxy, chloro, bromo, iodo or trifluoromethyl, $R_{10}$ is 1H-imidazol-1-yl or morpholinyl, and $R_{11}$ is $C_1$-$C_3$alkyl or unsubstituted phenyl or phenyl which is monosubstituted by $C_1$-$C_3$alkyl, halogen or trifluoromethyl, and the other substituents $R_5$, $R_6$, $R_7$ and $R_8$ are hydrogen, or a pharmaceutically acceptable salt thereof.

2. Method according to claim 1, wherein at least two of the substituents $R_5$, $R_6$ and $R_8$ in the compound of formula I are hydrogen.

3. Method according to claim 1, wherein each of the substituents $R_5$, $R_6$ and $R_8$ in the compound of formula I are hydrogen.

4. Method according to claim 1, wherein $R_1$, $R_2$, $R_4$, $R_5$, $R_6$ and $R_8$ in the compound of formula I are each hydrogen, $R_3$ is 2-pyridyl, 3-pyridyl, 4-pyridyl, 2-methyl-3-pyridyl, 4-methyl-3-pyridyl, 2-furyl, 5-methyl-2-furyl, 2,5-dimethyl-3-furyl, 2-thienyl, 3-thienyl, 5-methyl-2-thienyl, 2-phenothiazinyl, 4-pyrazinyl, 2-benzofuryl, N-oxido-2-pyridyl, N-oxido-3-pyridyl, N-oxido-4-pyridyl, 1H-indol-2-yl, 1H-indol-3-yl, 1-methyl-1H-pyrrol-2-yl, 4-quinolinyl, 1-methylpyridinium-4-yliodide, dimethylaminophenyl or N-acetyl-N-methylaminophenyl, and $R_7$ is $C_1$—$C_6$alkyl, $C_1$—$C_3$alkoxy, chloro, bromo, iodo, trifluoromethyl, hydroxy, phenyl, amino, mono($C_1$-$C_3$alkyl)-amino, di($C_1$-$C_3$alkyl)amino, $C_2$-$C_4$alkanoyl, propenyloxy, carboxy, carboxymethoxy, ethoxycarbonylmethoxy, sulfanilamido, N,N-di($C_1$-$C_3$alkyl)sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethylbenzyl or a radical of one of the formulae:

—$CO_2$R, —NH—C(=O)—R, —N(R)—C(=O)—R, —O—($CH_2$)$_n$—N(R)—R, —C(=O)—NH—($CH_2$)$_n$—N(R)—R, —CH($CH_3$)—NH—CHO, —C($CH_3$)=N—OH, —C($CH_3$)=N—O—$CH_3$, —C($CH_3$)—$NH_2$, —NH—$CH_2$—C(=O)—N(R)—R,

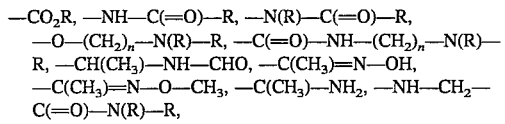

—($CH_2$)$_m$—$R_{10}$, —X—($CH_2$)$_m$—$R_{10}$ or

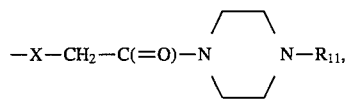

wherein R is $C_1$-$C_3$alkyl, X is oxygen or sulfur, m is 1, 2 or 3, n is 2 or 3, $R_9$ is hydrogen, $C_1$-$C_3$alkyl, $C_1$-$C_3$alkoxy, chloro, bromo, iodo or trifluoromethyl, $R_{10}$ is 1H-imidazol-1-yl or morpholinyl, and $R_{11}$ is $C_1$-$C_3$alkyl or unsubstituted phenyl or phenyl which is monosubstituted by $C_1$-$C_3$alkyl, halogen or trifluoromethyl.

5. Method according to claim 1, wherein $R_1$, $R_2$, $R_4$, $R_5$, $R_6$ and $R_8$ are each hydrogen, $R_3$ is 3-pyridyl, and $R_7$ is 1H-imidazol-1-yl, amino, trifluoromethyl, chloro or a radical of formula —$CO_2$R or —C(=O)—NH—($CH_2$)$_n$—N(R)—R, wherein each R is hydrogen or methyl and n is 3.

6. Method according to claim 1, wherein the compound of formula I is N-(3-1H-imidazol-1-ylphenyl)-4-(3-pyridyl)-2-pyrimidinamine or a pharmaceutically acceptable salt thereof.

7. Method according to claim 1, wherein the compound of formula I is N-(3-trifluoromethylphenyl)-4-(3-pyridyl)-2-pyrimidinamine or a pharmaceutically acceptable salt thereof.

8. Method according to claim 1, wherein the compound of formula I is N-(3-chlorophenyl)-4-(3-pyridyl)-2-pyrimidinamine or a pharmaceutically acceptable salt thereof.

9. Method according to claim 1, wherein the compound of formula I is N-(3-aminophenyl)-4-(3-pyridyl)-2-pyrimidinamin or a pharmaceutically acceptable salt thereof.

10. Method according to claim 1, wherein the compound of formula I is N-(3-methoxycarbonylphenyl)-4-(3-pyridyl)-2-pyrimidinamine or a pharmaceutically acceptable salt thereof.

11. Method according to claim 1, wherein the compound of formula I is N-(3-[3-aminopropylaminocarbonyl]phenyl)-4-(3-pyridyl)-2-pyrimidinamine or a pharmaceutically acceptable salt thereof.

* * * * *